United States Patent
Iwashima et al.

(10) Patent No.: US 9,029,139 B2
(45) Date of Patent: May 12, 2015

(54) OMENTUM AS A SOURCE OF STROMAL/STEM CELLS AND MEDICAL TREATMENT USING STROMAL/STEM CELLS

(75) Inventors: Makio Iwashima, River Forest, IL (US); Robert Love, Elmhurst, IL (US); Rudolf Karl Braun, Madison, WI (US); Perianna Sethupathi, Wheaton, IL (US); Katherine Lathrop Knight, Chicago, IL (US)

(73) Assignee: Loyola University of Chicago, Maywood, IL (US)

( * ) Notice: Subject to any disclaimer, the term of this patent is extended or adjusted under 35 U.S.C. 154(b) by 601 days.

(21) Appl. No.: 12/730,701

(22) Filed: Mar. 24, 2010

(65) Prior Publication Data
US 2011/0081321 A1    Apr. 7, 2011

Related U.S. Application Data

(60) Provisional application No. 61/163,263, filed on Mar. 25, 2009, provisional application No. 61/241,996, filed on Sep. 14, 2009.

(51) Int. Cl.
| | |
|---|---|
| C12N 5/00 | (2006.01) |
| C12N 5/071 | (2010.01) |
| C12N 5/074 | (2010.01) |
| A01N 63/00 | (2006.01) |
| C12N 5/0775 | (2010.01) |
| A61K 35/12 | (2006.01) |

(52) U.S. Cl.
CPC ............... *C12N 5/0667* (2013.01); *A61K 35/12* (2013.01)

(58) Field of Classification Search
CPC ..... A61K 35/12; A61K 35/545; A61K 35/28; A61K 35/35; C12N 5/0667; C12N 5/0668; C12N 5/0662; C12N 5/0623
See application file for complete search history.

(56) References Cited

U.S. PATENT DOCUMENTS

2006/0051327 A1*   3/2006   Johnson ................ 424/93.7

FOREIGN PATENT DOCUMENTS

WO    2005028626    3/2005

OTHER PUBLICATIONS

Singer et al. (Cancer Immunol. Immunother. 2001 60:425-431).*
Janeway et al. (Immunobiology: The Immune System in Health and Disease. 5th ed. New York: Garland Science: 2001, Fig. 8.31).*
Kawai and Akira (Seminars in Immunol. 2007 19:24-32).*
Singh et al. (Cell Tissue Res. Jan. 15, 2008, 332: 81-88).*
Keyser et al. (Cell Transplantation 2007, 16: 555-562).*
Vernik and Singh (Int. J. Artificial Organs 2007 30(2): 95-99).*
Singh et al. (BBRC Feb. 5, 2007, 355: 258-262).*
Singh et al. (World J. Gastroenterology Mar. 7, 2009, 15(9): 1057-1064).*
Litbarg, N.O. et al., "Activated omentum becomes rich in factors that promote healing and tissue regeneration". Cell Tissue Res., 2007, vol. 328, pp. 487-497.
Kuypers, F.A. et al., "Stem cell transplantation with S-59 photochemically treated T-cell add-backs to establish allochimerism in murine thalassemia". Ann. N.Y. Acad. Sci., 2005, vol. 1054, pp. 214-222.
Levicar, N. et al., "Stem cells as a treatment for chronic liver disease and diabetes". HEP, 2007, vol. 180, pp. 243-262.

* cited by examiner

*Primary Examiner* — Peter J Reddig
(74) *Attorney, Agent, or Firm* — Hartman Global IP Law; Gary M. Hartman; Michael D. Winter

(57) ABSTRACT

Methods for generating and using omentum cells, and particularly stromal cells and/or omentum stem cells, in medical treatments such as tissue repair and regeneration to facilitate healing from traumatic injury to an abdominal organ, and immune modulation treatments such as suppression of immune responses and inflammation and prevention of tissue fibrosis. According to one aspect, a medical procedure is performed on a patient that involves harvesting omental tissue from the patient, and then transferring the omental tissue to an organ of the patient. At least a portion of the harvested omental tissue may be activated prior to transferring the omental tissue to the organ. Alternatively, the transferred omental tissue may comprise non-lymphoid cells isolated from the omentum tissue and obtained by homogenizing at least a portion of the harvested omental tissue. The invention also encompasses a medical procedure comprising the transfer of omental stem cells to a patient, and a procedure comprising in vitro activation of omental stem cells by T cells to enhance immunomodulatory functions of the omental stem cells.

4 Claims, 12 Drawing Sheets

OMENTUM AS A SOURCE OF STROMAL/STEM CELLS AND MEDICAL TREATMENT USING STROMAL/STEM CELLS

CROSS REFERENCE TO RELATED APPLICATIONS

This application claims the benefit of U.S. Provisional Application No. 61/163,263, filed Mar. 25, 2009, and U.S. Provisional Application No. 61/241,996, filed Sep. 14, 2009. The contents of these prior patent documents are incorporated herein by reference.

BACKGROUND OF THE INVENTION

The present invention generally relates to medical procedures and treatments involving the use of the omentum. More particularly, the present invention relates to the use of the omentum as a source of stromal/stem cells for use in tissue repair, tissue regeneration and immune modulation treatments.

The omentum is a highly vascular, fatty tissue approximately fourteen inches long and ten inches wide that hangs like an apron over the intestines and lower abdominal area of humans and animals. Although the omentum had been viewed as an inert tissue bereft of significant biological function, scientists are now discovering that it is an intriguing, physiologically dynamic tissue with a considerable body of research that supports its therapeutic potential. Following a traumatic injury of an internal organ in the abdominal cavity, the omentum is known to migrate to the injured site, adhere to the wound, and promote healing. Surgical transposition of the omentum to a site of injury, for example, an ischemic heart, fractured bone or injured spinal cord, has also been shown to facilitate organ regeneration. Surgical transposition of the omentum has also been used in lung transplantation to increase vascularization and improve healing of the bronchial anastomosis. Furthermore, omental areas called "milky spots" are known to be capable of generating specialized immune cells that facilitate healing. There is also speculation that the migration of omental immune cells can help repair injured spinal cords.

It is believed that prior to the present invention, a possible role in the repair and/or regeneration of tissue injury had not been previously ascribed to omentum cells, and there was no clear knowledge regarding a possible immunomodulatory role for omentum cells.

BRIEF DESCRIPTION OF THE INVENTION

The present invention provides methods for generating and using omentum cells, and particularly stromal cells and/or omentum stem cells (collectively referred to as OSCs), in medical treatments including but not limited to tissue repair and regeneration, for example, to facilitate healing from traumatic injury to the liver and pancreas, and immune modulation treatments including but not limited to suppression of immune responses and inflammation and prevention of tissue fibrosis.

According to a first aspect of the invention, a medical procedure is performed on a patient that involves harvesting omental tissue from the patient, and then transferring the omental tissue to an organ of the patient. Optionally, at least a portion of the harvested omental tissue may be activated prior to transferring the omental tissue to the organ. Alternatively, the transferred omental tissue may comprise non-lymphoid cells isolated from the omentum tissue and obtained by homogenizing at least a portion of the harvested omental tissue.

This aspect of the invention can be used for the purpose of repairing and regenerating damaged tissue, instead of treating disease symptoms or relying on organ transplants. Potential applications include the regeneration of various organs and tissues, including but not limited to the liver and pancreas. The ability to regenerate any type of tissue would be of extraordinary value.

Other aspects of the invention include a medical procedure that is performed on a patient and comprises the transfer of omental stem cells to the patient, and a procedure that involves in vitro activation of omental stem cells by T cells to enhance immunomodulatory functions of the omental stem cells.

According to these aspects of the invention, omental stem cells have been unexpectedly found to have a strong anti-immune response/inflammatory function and promote tissue regeneration in a lung fibrosis model. Consequently, though there was previously no functional characteristic known for the omentum with regard to immune modulation or lung repair, additional significant benefits of the invention include immune response modulation associated with autoimmune disorders and lung fibrosis, for example, to suppress immune responses and help lung regeneration.

From the above, it should be apparent that another notable aspect of the invention is the ability to directly harvest omental stem cells from a patient or donor. Alternatively, omental stem cells can be harvested as groups of cells that attach/bind to inert foreign material placed in the abdomen of a donor. Following implantation (for example, after a period of seven to ten days), the beads and binding cells can be collected. The cells can be dispersed in vitro by collagenase treatment, and then live cells can be purified and injected into the host intravenously. Whether harvested directly or collected, omental stem cells isolated from a patient's omentum offer the advantage of eliminating the concern for rejection. Yet another notable aspect is to activate omental stem cells in vitro by T cells, macrophages, or a Toll-like receptor (TLR) ligand such as lipopolysaccharide (LPS) to enhance their immunomodulatory functions prior to in vivo injection.

Other aspects and advantages of this invention will be better appreciated from the following detailed description.

denotes a statistical difference from the "Normal" or "Omentx" or "Inact oment" groups at P<0.05. A "b" denotes a statistical difference from day three and day seven groups at P<0.05. With regard to the "Omentx" and "Inact oment" groups, no differences were seen at 3 d, 7 d, 14 d and 28 d compared to the "Normal" group (only day fourteen data is shown; n=3).

Figure 3:
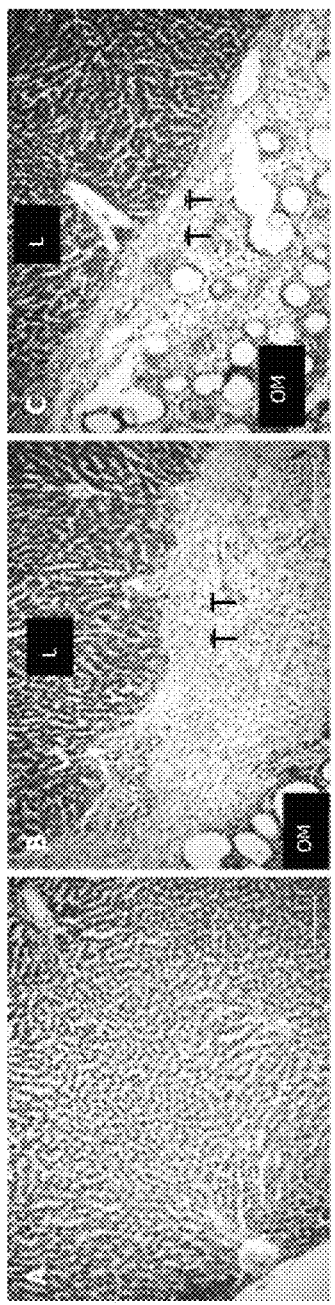

FIG. 3 contains scanned images of the histology of the boundary between the growing edge of a liver and an activated omentum (trichrome stained). Image A is of a "Normal" rat liver. Image B shows a liver and omentum separated by a wide and compact interlying tissue (400-600 μm) at 7 d after injury. The interlying tissue (T) is between the liver tissue (L) and the omental tissue (OM) with embedded polydextran gel particles. Occasionally, islands of liver tissue were observed in the interlying tissue (FIG. 4G). The compactness and the width of the interlying tissue was maximal between 3 d and 7 d after liver injury (Image B), and became thinner (100-150 μm) and looser by 14 d (Image C). By 28 d the interlying tissue was barely appreciable and appeared similar to a tissue septum (picture not shown). The horizontal white bar in the pictures represents 100 μm.

Figure 4:
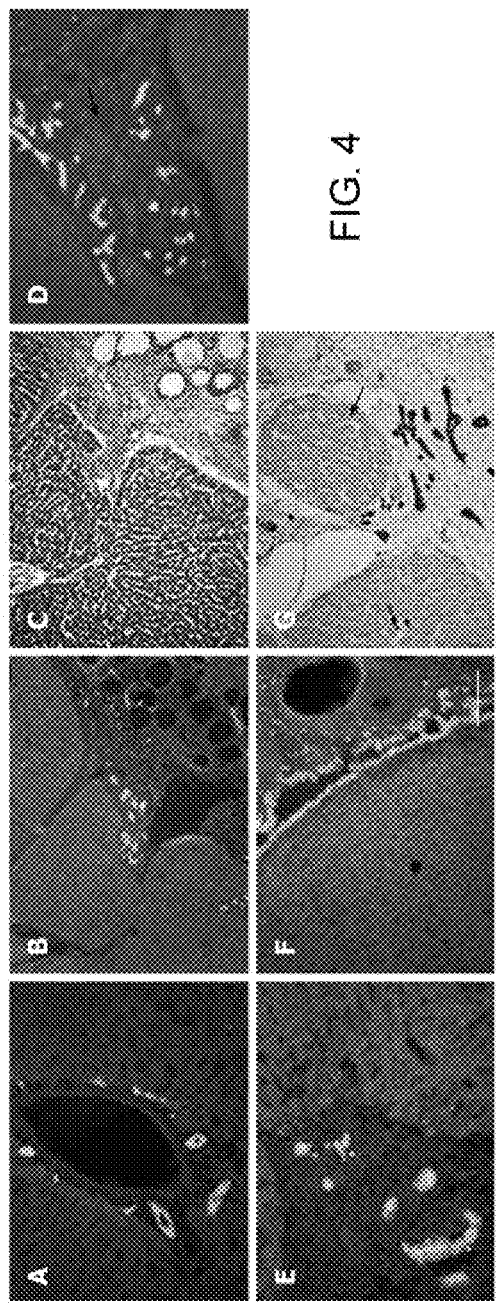

FIG. 4 contains scanned images of normal and regenerated rat liver (from activated omentum) immunostained for cytokeratin-19, a marker of oval cells. Image A is of a normal uninjured liver lobe showing the widespread presence of oval cells in the lining of bile ducts lying around a central vein. Images B, D, E and G are of different areas of an injured liver showing extensions of cytokeratin-19 positive bile ducts in the interlying tissue between the liver and the activated omentum. Image C shows the tissue section of Image B stained with trichrome to show the bile ducts lying in the interlying omental tissue. As seen in Image F, on occasion the growing edge of the liver lying in the interlying tissue was observed to be entirely covered with cytokeratin-19 positive cells. In Image G, islands of liver tissue, probably newly formed, are seen in the interlying tissue (black arrows; also seen in Image D). Images A, B, D, E and F were stained by immunofluorescence. Image G was stained by immunoperoxidase. The horizontal white bar in F represents 100 μm for all pictures.

Figure 5:
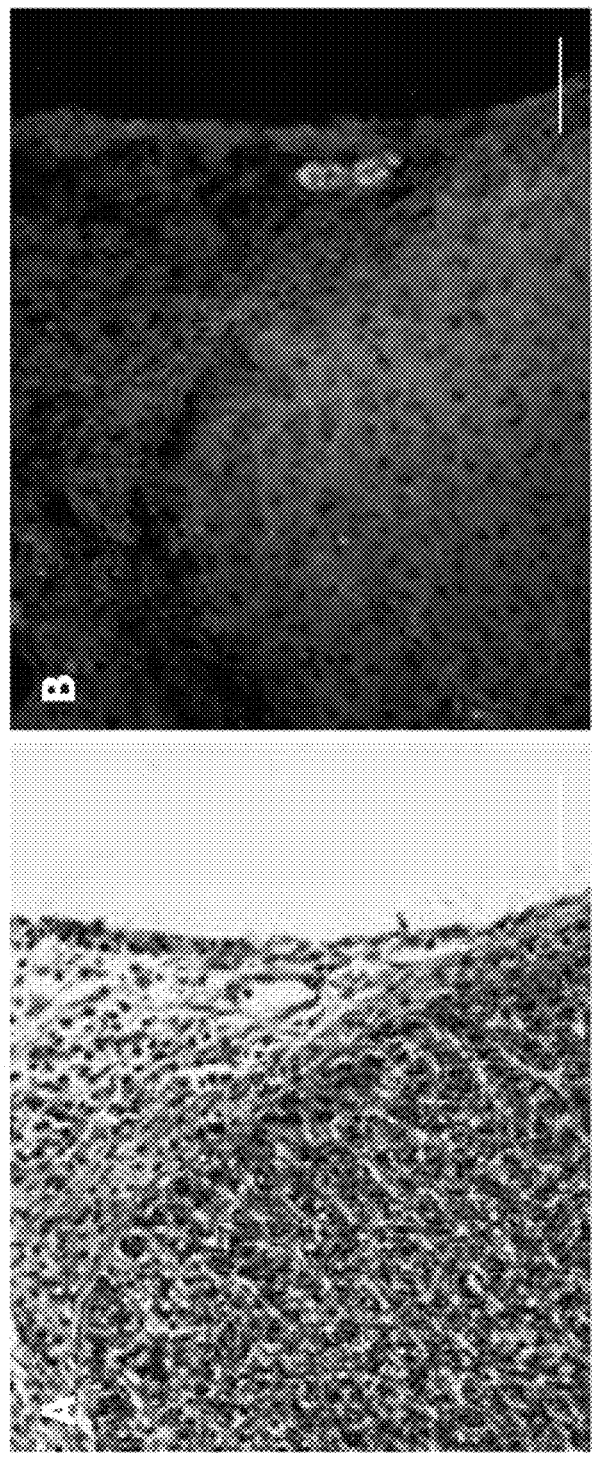

FIG. 5 contains two scanned images showing the histology and cytokeratin-19 immune staining of a liver at the boundary between the growing edge of the liver and inactivated omentum at day three or seven after injury. Image A is a trichrome-stained section showing the adherent omental tissue with a thinner interlying tissue than that seen in the activated omentum group (FIG. 3 for comparison). In Image B, cytokeratin-19 positive bile ducts are seen in the interlying tissue (same section as Image A), although these were much less frequent than those seen in the activated omentum group (FIG. 3 for comparison). The horizontal white bars in Images A and B represent 100 μm.

Figure 6:
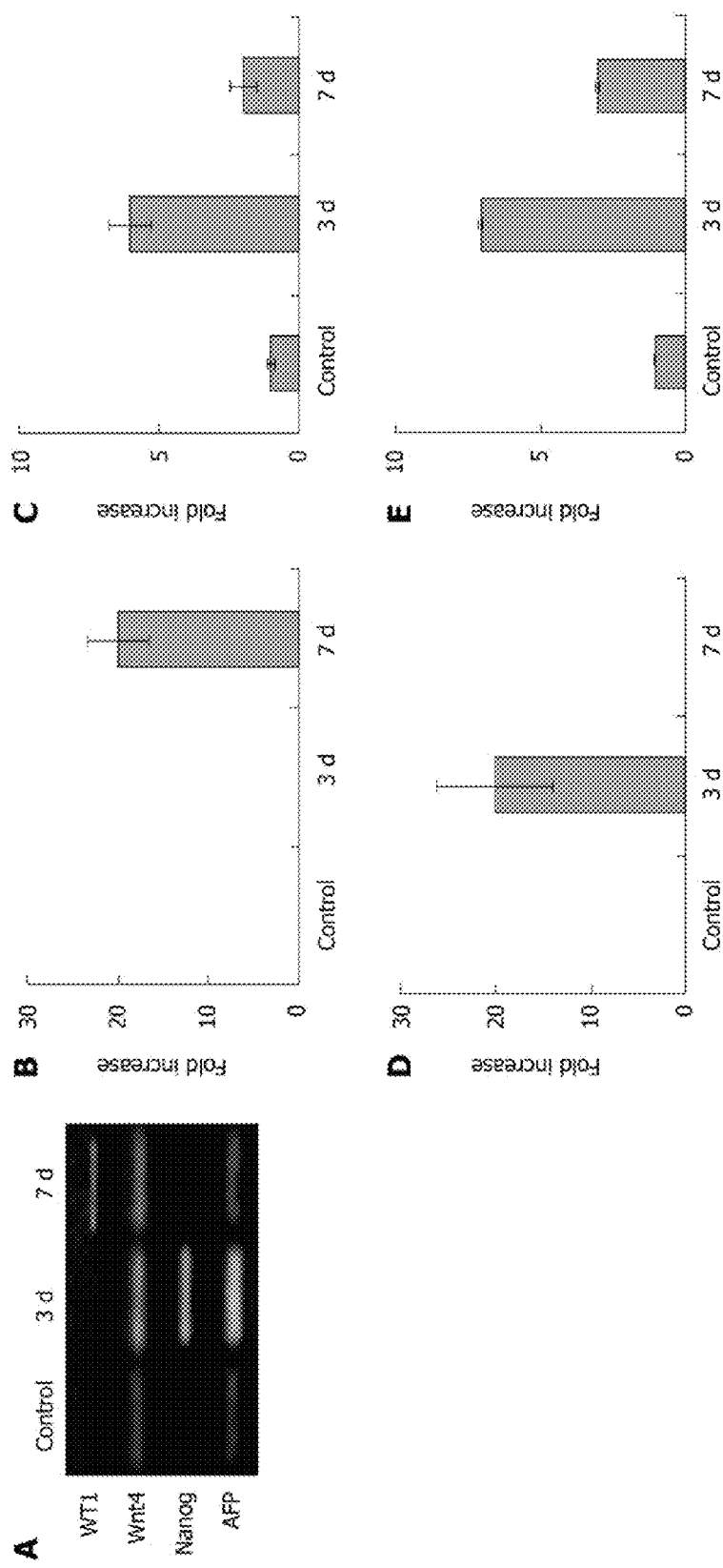

FIG. 6 evidences the activation of developmental genes in a regenerated liver at the wound site at days three and seven after injury and fusion of the activated omentum. As seen in Image A, the regenerating part of the liver (part of liver attached to the omentum) showed high expression levels (7 to 20-fold) of WT-1, Wnt-4, Nanog, AFP by RT-PCR compared with normal rat adult liver tissue ("Control"). Images C, D and E show that Wnt-4, Nanog and AFP, respectively, were maximally activated at day 3, while Image B shows maximal activation of WT-1 at day 7. Tissue from a regenerated liver taken from sites farther away from the wound area (about 0.5 cm and about 1.0 cm away in the same lobe and in an uninjured lobe) showed reduced activation of WT-1, Wnt-4 and AFP genes (although higher in all cases compared with normal adult liver), suggesting that the regeneration stimulus 'rippled' throughout the liver from the wound area (data not shown). n=3 in each bar and the differences amongst the bars within each of FIGS. 6B, 6C, 6D, and 6E are statistically significant (P<0.05).

Figure 7:
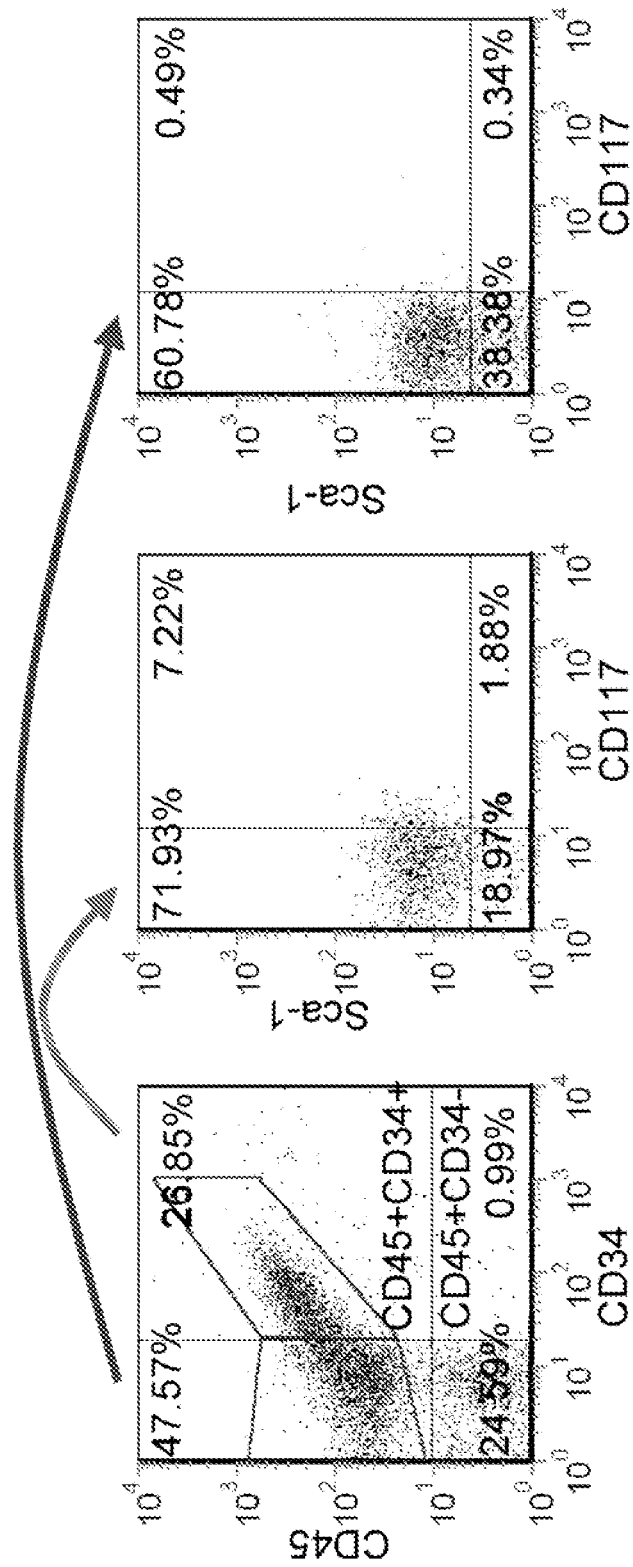

FIG. 7 evidences the heterogeneity of omental cells. Mouse omentum was activated by intraperitoneal injection of about 1 ml of sterile slurry of polydextran beads and removed 5 days after the injection. Cells were isolated by disrupting the tissue and digesting with collagenase type I followed by a Ficoll density gradient centrifugation. After staining with anti-CD34-PE, anti-Sca-1-PerCP-Cy5.5, anti-CD45-APC-Alexa750, and anti-CD117-APC, cells were analyzed on a CyFlow ML cytometer (Partec Inc., NJ) and analyzed for the expression of the specific surface antigens. Dead cells were labeled using the dead cell staining kit from Invitrogen. Non-specific staining was blocked by incubating the cells with rat-IgG prior to the specific staining.

Figure 8:
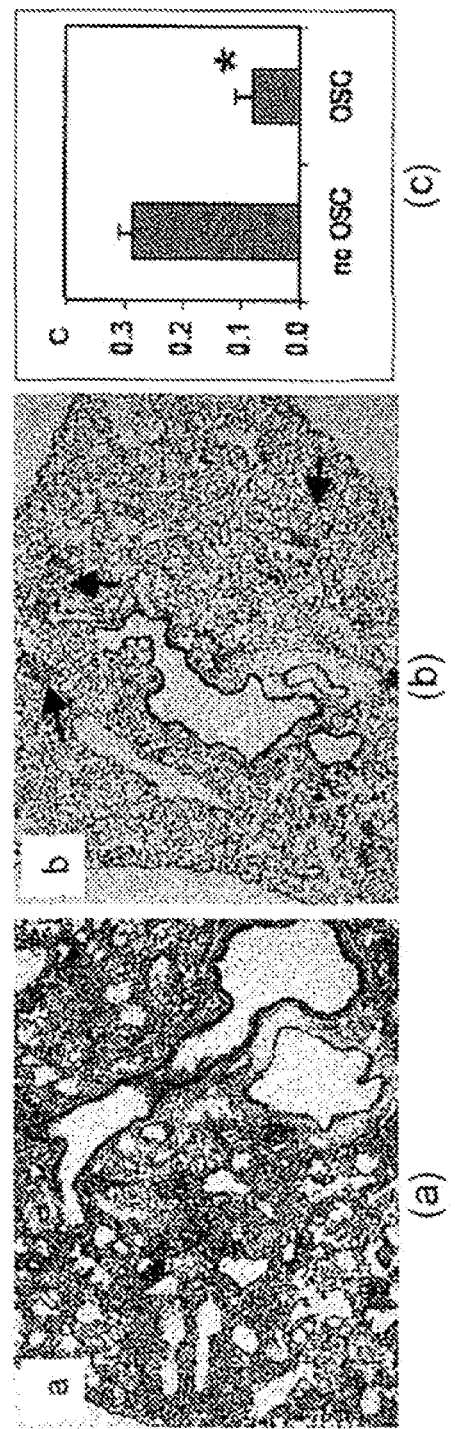

FIG. 8 is a bar chart evidencing a protective effect experimentally shown to be provided by OSCs against bleomycin-induced lung injury. Bleomycin was H&E stained 5 μm section of paraformaldehyde fixed lungs twelve days after bleomycin instillation. FIG. 8a is an image of a control lung that received bleomycin without a transfer of OSCs. FIG. 8b is an image of a lung that received a transfer of $10^6$ OSCs by intraperitoneal injection four hours after bleomycin instillation. FIG. 8c is a graph comparing the volume density of lesion for bleomycin-injured lungs that received either a transfer of saline ("no OSC") or a transfer of OSCs ("OSC"). Parenchymal lesions are defined as a thickening of interalveolar septa due to edematous swelling, inflammatory cells, or fibrosis associated with hyperplastic epithelial cells, and/or clusters of airway inflammatory cells in either airways or interstitium. Lesions were evaluated in a single section from each of the sampled lungs. The volume density of lesion, $V_V$, was determined by point counting techniques using the formula $V_V=P_P=P_N/P_T$ where $P_P$ is the point fraction of $P_N$, the number of points hitting a lesion divided by $P_T$, the total number of points hitting the section. Because of the patchy distribution of the lesion, each section was systematically scanned at a final magnification of 20× with a 25-point lattice test system until all fields (five to twenty-five fields) in the section were evaluated. A mean volume density of lesion was obtained by averaging the $V_v$ values contributed by each lung.

Figure 9:
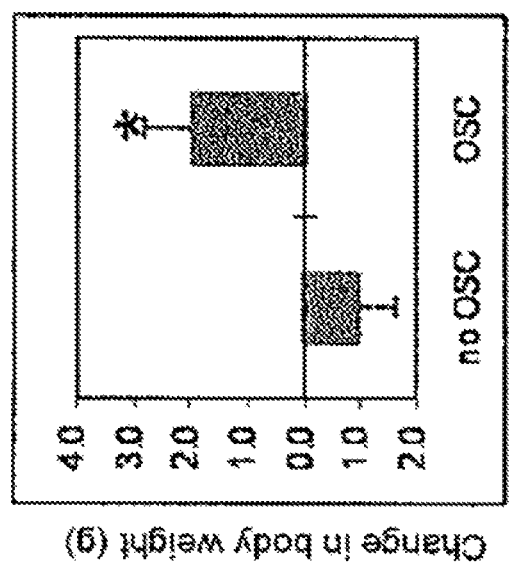

FIG. 9 is a bar chart evidencing another beneficial effect experimentally shown to be provided by OSC, reflected by weight loss/gain in mice after bleomycin instillation. The chart is based on data obtained seven days after bleomycin instillation and either intraperitoneal injection of saline ("no OSC") or adoptive transfer of OSCs ("OSC"). The omentum was activated by injecting about 1 ml polydextran slurry intraperitoneally. The omentum was removed seven days later and cells were purified by collagenase treatment and density gradient centrifugation. $10^6$ OSCs were injected intraperitoneally about four hours after bleomycin instillation. The * symbol is used to indicate a significant difference (p<0.001).

Figure 10:
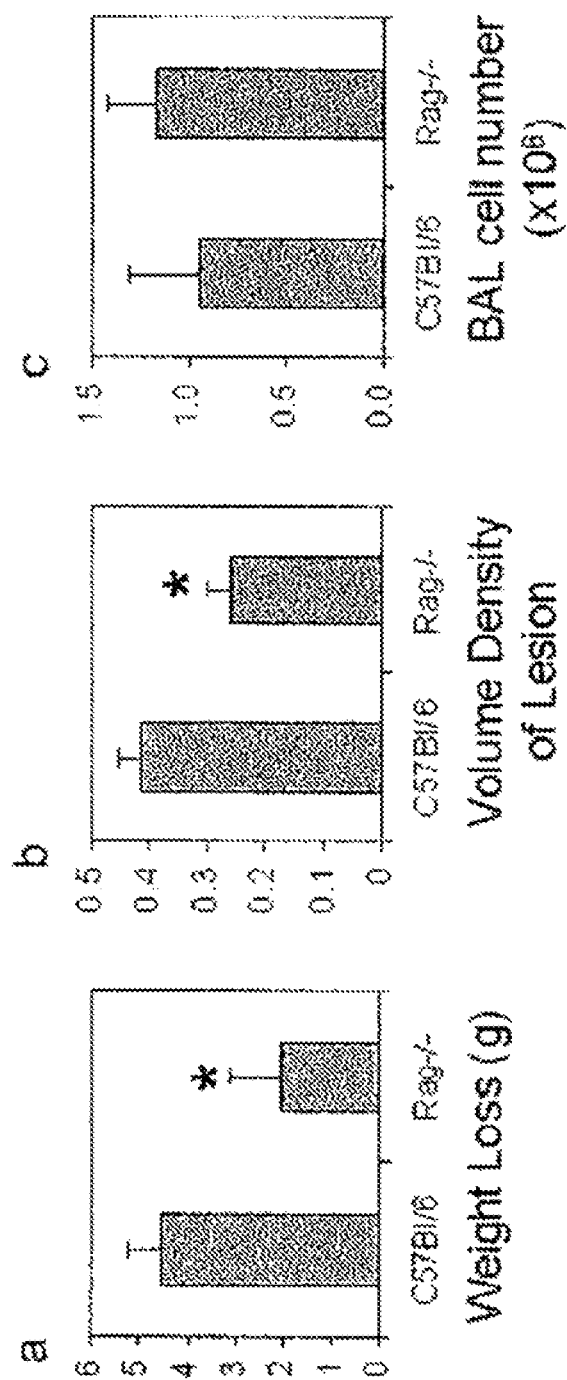

FIG. 10a-c contains bar graphs plotting experimental data, and by which lung inflammation after bleomycin instillation is shown to be T cell dependent. Bleomycin (0.04 U) was instilled intratracheally into lymphocyte deficient Rag-/- and C57Bl/6 wild type mice. The experiment was discontinued eleven days after injury because of the severe weight loss of the wild type mice. Mice were weighed, their lungs lavaged, and the cell number in the bronchoalveolar lavage (BAL) fluid was counted to acquire the data represented in FIG. 10.

Figure 11:
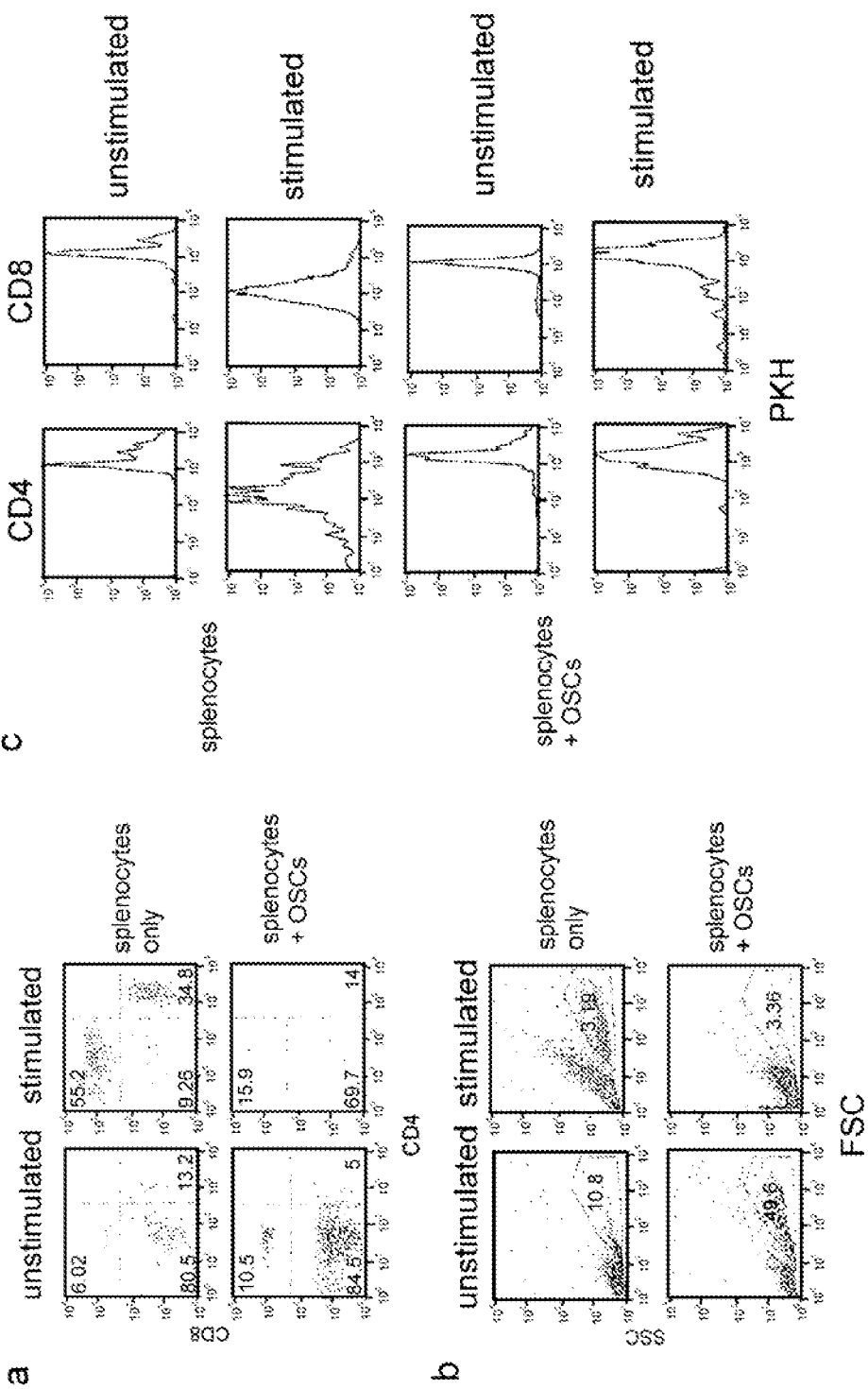

FIG. 11 contains plots evidencing the ability of activated T cells to induce an immunomodulatory function in OSCs. Total splenocytes were cultured for three days in vitro with or without OSCs (1:1 cell ratio). Anti-CD3 antibody (stimulated) or isotype control IgG (unstimulated) was added to the culture along with IL-2. Numbers within the plots indicate relative frequency of cells in each quadrangle. The plots contain representative data from three independent experiments: (a) CD4 and CD8 expression by live cell gated population; (b) size gating based on forward scatter (FSC) and size scatter (SSC) gate for live cells (frequency for each sample is shown); and (c) proliferation of CD4 and CD8 T cells. Prior to the co-culture with OSCs, splenocytes were stained with PKH26. This dye stains the cell membrane. As cells divide, the level of PKH decreases.

FIG. 12a shows that IFN-gamma is required for induction of immunoregulatory functions by OSCs. Splenic T cells were stimulated in the manner described for FIG. 11 with anti-CD3 antibody in the presence (middle panel) or absence (left panel) of OSCs. To test the role of IFN-gamma and inducible nitric oxide synthase (iNOS) in OSC function, anti-IFN-gamma antibody or iNOS inhibitor (L-NAME) was added to the culture of OSCs and activated splenocytes (right panels). Proliferation of T cells were determined by the level of PKH26 staining as described for FIG. 11. Numbers in FIG. 12a show the percentage of cells that underwent cell division. FIG. 12b shows that iNOS expression is induced by IFN-gamma in OSCs. Macrophage cell line, OSCs, or total splenocytes were stimulated with IFN-gamma (+) or left unstimulated (−) for one day. Total cell lysates were made from these cells and analyzed by Western blot using anti-iNOS antibody (upper panel) or anti-b-active antibody (lower panel).

Figure 13:
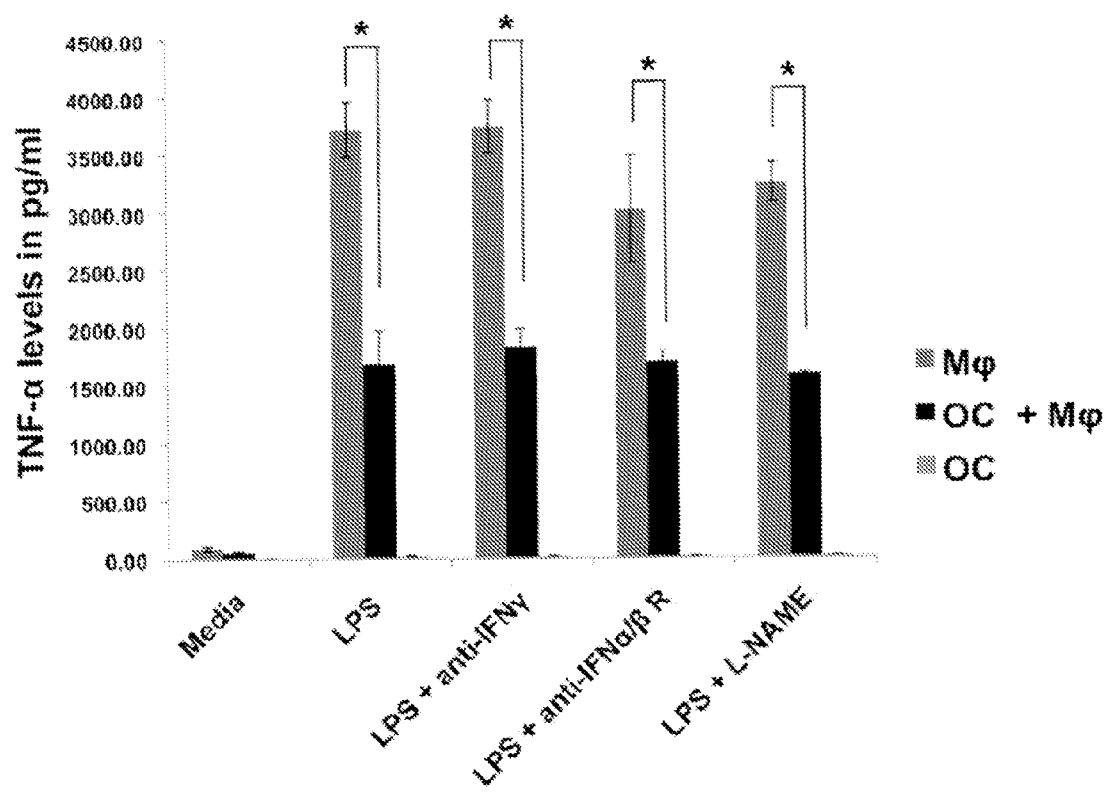

FIG. 13 shows that OSCs have the potent suppressive functions against macrophages to produce TNF-alpha. A macrophage cell line (mψ), OSCs and macrophage (mψ+OC), or OSCs alone (OC) was left unstimulated (media) or stimulated by LPS for 24 hours (LPS). To this culture were added blocking antibody against IFN-gamma, IFN-alpha and beta, or inhibitor of iNOS (L-name). After about eighteen hours, culture supernatant were analyzed for the level of TNF-alpha by ELISA.

DETAILED DESCRIPTION OF THE INVENTION

In the following discussion, reference will be made to the activation of omental cells by placing (implanting or injecting) inert foreign matter, such as polydextran particles or polyvinylchloride (PVC) tubing, in the abdominal cavity. In investigations described below, activation of omentum was demonstrated with two types of foreign matter: polydextran beads in an amorphous slurry, or a PVC pipe (which induces the omentum to take a specific shape). Activation of the omentum by implantation/injection of inert foreign matter causes the omentum to grow and surround the solid matter. Furthermore, the increased mass of the omentum comes from proliferation of milky spots containing stromal cells, interstitial cells, and blood vessels, and not the fat cells that comprise the omentum in its resting state. As described below, the activated omentum cells can be later harvested from the activated omentum and transposed to an injured or diseased abdominal organ site, for example, a liver damaged from injury or disease, or a diabetic pancreas. No immunosuppression is required because self-omentum cells can be used. As such, a notable aspect of the invention is the ability to provide a readily available source of stem cells for cell therapy using autologous cells that will not be rejected by the recipient.

While it has already been established that surgically transposing the omentum to the site of injury facilitates organ regeneration, the activated state of the omentum enables the invention to substantially improve on prior techniques using nonactivated omentum as a result of activated omentum supplying injured tissue with angiogenic, growth, and chemotactic factors that facilitate healing. As will become evident from the following discussion, activated omentum transpositions have the ability to repair acutely damaged liver and pancreas tissue. The former is significant because, while liver can regenerate itself upon severe injury, less-than-severe trauma is more common and clinical recovery from less-than-severe liver injury is quite difficult. The latter is significant because regeneration of pancreas tissue and insulin-producing islets can be explored as a treatment for diabetes.

In an investigation leading to the present invention and reported in Singh et al., "Stromal Cells Cultured from Omentum Express Pluripotent Markers, Produce High Amounts of VEGF, and Engraft to Injured Sites," Cell Tissue Res., 332 (1):81-8 (April 2008), whose contents are incorporated herein by reference, rat omentum activated by intraperitoneal injection of inert polydextran particles was found to be rapidly surrounded by cells that express markers of adult stem cells (SDF-1 alpha, CXCR4, WT-1) and of embryonic pluripotent cells (Oct-4, Nanog, SSEA-1). Such cells were cultured and found to retain stem cell markers and produce high levels of vascular endothelial growth factor for up to ten passages. After systemic or local injection of these cultured cells into rats with acute injury of various organs, the cells were found to specifically engraft at the injured sites. For example, omentum cells were shown to migrate specifically to an ischemia-injured kidney but not to the uninjured contralateral kidney. In addition, these omentum cells were found to secrete high levels of vascular endothelial growth factor, which is known to be proangiogenic. Such research evidenced that omental stromal cells can be cultured from activated omentum and exhibit stem cell properties, enabling them to be used for repair and possibly for regeneration of damaged tissues.

A first series of investigations were conducted to explore the mechanism of liver regeneration induced by fusing the omentum to a small traumatic injury created in the liver. Because liver regeneration can be brought about by resident stem cells (oval cells) even in the absence of hepatocyte multiplication, the investigation was an attempt to use activated omentum to facilitate liver regeneration. For this investigation, reported in Singh et al., "Omentum Facilitates Liver Regeneration," World Journal of Gastroenterology (Mar. 7, 2009) 15(9): 1057-1064 (the contents of which are incorporated herein by reference), a small wedge wound was made in the livers of three groups of rats. A first group was omentectomized, while in a second group the omentum was left in situ and not activated. In the third group, the omentum was activated by polydextran beads in an amorphous slurry. The activated omentum and polydextran beads were placed in the small wedge wounds of the third group of rats to allow the omentum to fuse to the wound. Regeneration of the liver was monitored by determining the ratio of liver weight/body weight, by histological evaluation (including immune staining for cytokeratin-19, an oval cell marker), and by testing for developmental gene activation using reverse transcription polymerase chain reaction (RT-PCR).

As discussed in greater detail below, liver regeneration was not observed in the omentectomized rats, nor was there significant regeneration when the omentum was not activated even though the omentum was observed to have fused with the liver. In contrast, the livers of the third group of rats with the activated omentum expanded to a size of about 50% greater than its original size, and there was histologically an interlying tissue between the wounded liver and the activated omentum in which bile ducts, containing cytokeratin-19 positive oval cells, extended from the wound edge. In this interlying tissue, oval cells were abundant and appeared to proliferate to form new liver tissue. In rats pre-treated with drugs that inhibited hepatocyte growth, liver proliferation was ongoing, indicating that regeneration of the liver was the result of oval cell expansion. From this, activated omentum was concluded to have facilitated liver regeneration following injury by a mechanism that depends largely on oval cell proliferation. The investigation was further concluded to have shown that introducing a foreign body into the peritoneal cavity further enhances the healing power of the omentum by causing it to expand, surround the foreign body, and transform itself from a mostly fatty tissue to a tissue abundant in progenitor cells and rich in growth and angiogenic factors (activated omentum).

Figure 1:
FIG. 1 is a scanned image of a rat liver used in a traumatic liver injury model to induce regeneration. A wound was created in one of the lobes of the liver by removing a wedge of tissue (3-4 mm on each side) with a pair of fine scissors. The horizontal black bar in the picture represents three mm.

The animal experimentation performed in the investigation was conducted according to the approval of the Institutional Animal Care and Use Committee (IACUC). Under general anesthesia, the rats (male Sprague-Dawley rats, about 200 to 250 g) were laparotomized and the most anterior and prominent of the liver lobes lying in the middle of the abdominal cavity was exposed. Using a pair of fine scissors a small V-shaped cut was made in the lobe (3-4 mm on each side) and the wedge of liver was removed (FIG. 1) and later used as normal tissue for immunostaining and quantitative reverse transcription polymerase chain reaction (RT-PCR).

After removing the small wedge of tissue (resulting in a traumatic hepatic wedge injury), the omentum was allowed to adhere to the wound in order to supply the liver with stem cells. For the first two groups were controls in which the omentum was either left in its native state (inactivated omentum) or surgically removed (omentectomized) via an omentectomy, by which the entire omentum was surgically excised from the lower curvature of the stomach. For the first and second groups, the investigation focused on the cellular and developmental gene activation at the site of injury and omental adhesion. In the third group (activated omentum), before the incision was sutured, 5 mL of polydextran bead slurry (Biogel P-60, 120 µmol/L; Biorad Laboratories, Richmond, Calif., USA) (1:1 in normal saline) was introduced into the abdominal cavity to activate the omentum.

The animals were maintained on normal rat chow and water ad libitum from three to twenty eight days. At the time of sacrifice, the livers were examined, wholly removed, and weighed. Liver mass was expressed conventionally as a percent ratio: liver weight/body weight. Pieces of the re-grown liver from the point of omental fusion, and at 0.5 cm and 1.0 cm away from the wound as well as portions from an uninjured lobe were collected for immunostaining and quantitative RT-PCR.

To test whether liver regeneration by omental intervention depended upon hepatocyte proliferation, rats were injected intraperitoneally daily for four days with 2-acetyl-aminofluorene (2-AAF; 30 mg/kg dissolved in M400 polyethylene glycol (avg. MW=400); both chemicals were obtained from the Sigma Chemical Company, St Louis, Mo., USA) to inhibit hepatocyte proliferation, followed by liver wounding on the fifth day and, for the third group, omental activation by intraperitoneal injection of the polydextran bead slurry. Further daily injections of 2-AAF were performed for additional four days to inhibit expansion of hepatocytes. The rats were sacrificed twenty-eight days after liver wounding and the livers were examined, wholly removed, and weighed.

Pieces of normal and regenerated liver (including the omental attachment) were fixed for histology and immunostaining by immersion in Histochoice® (Amersco Inc., Solon, Ohio, USA). Following dehydration and paraffin embedment, tissues were sectioned (5 µm thick) and stained with hematoxylin-eosin (HE) or Trichrome stain. Immunostaining was carried out by first pressure-cooking the sections for ten minutes in a solution of BorgDecloaker® (Biocare Medical; Walnut Creek, Calif., USA) for antigen enhancement. For immunofluorescent staining, the sections were incubated with monoclonal (mouse) anti-rat cytokeratin-19 (Sigma Chem. Co, St Louis, Mo., USA) followed by washing and reincubating with fluorescein (FITC) labeled anti-mouse IgG antibody (Sigma Chem. Co., St Louis, Mo., USA). The slides were washed and wet-mounted in glycerol-PBS. For immunoperoxidase staining, sections were sequentially incubated with monoclonal (mouse) anti-rat cytokeratin-19, anti-mouse IgG-biotin conjugate, avidin-horse radish peroxidase and finally developed with diaminobenzidine-$H_2O_2$ (brown color) (Vector Laboratories, Inc., Burlingame, Calif., USA). The slides were examined either by epifluorescent or light microscopy and digitally photographed (Nikon Inc., New York, N.Y., USA).

Liver tissues at the point of omental attachment or wound edge (in omentectomized rats), at about 0.5 and about 1.0 cm away from the omental attachment, and from a remote uninjured lobe were tested for expression of developmental genes. The liver tissue was cleared of the attached omental tissue and processed for total RNA extraction by Trizol using a RNA purification kit (Invitrogen, CA, USA). The RT-PCR procedure was carried out in one step using 3 µg of total tissue RNA and primers using the Invitrogen RT-PCR system (Invitrogen, CA, USA). The system used Superscript II reverse transcriptase for first strand synthesis and Taq DNA polymerase for second strand cDNA synthesis and amplification (30 cycles). β-actin amplification was performed from the total RNA preparations (60 ng) as a control. The RT-PCR products were quantitated as the ratio of gene band density/β-actin band density by image analysis using MIPAV software (JAVA imaging software inspired by the National Institutes of Health). Quantitative data presented in FIGS. 2 through 6, which compare the differences between the different rat groups, were analyzed by student's t test. The differences were considered statistically significant if P was less than 0.05.

In all rats in which the liver was traumatically wounded and the omentum remained intact, whether activated (n=24) or inactivated (n=12), there was fusion between the omentum and the wound edge of the liver and the omentum remained attached to the injury site through day twenty-eight. On gross inspection, by day fourteen new tissue filled the resected wedge, and the location of the resection site was only identifiable by the omental attachment. In omentectomized rats (n=12), there was an absence of omental attachment and of liver growth at the wound, making the wound edges noticeable through day twenty-eight (see FIG. 1).

Figure 2:
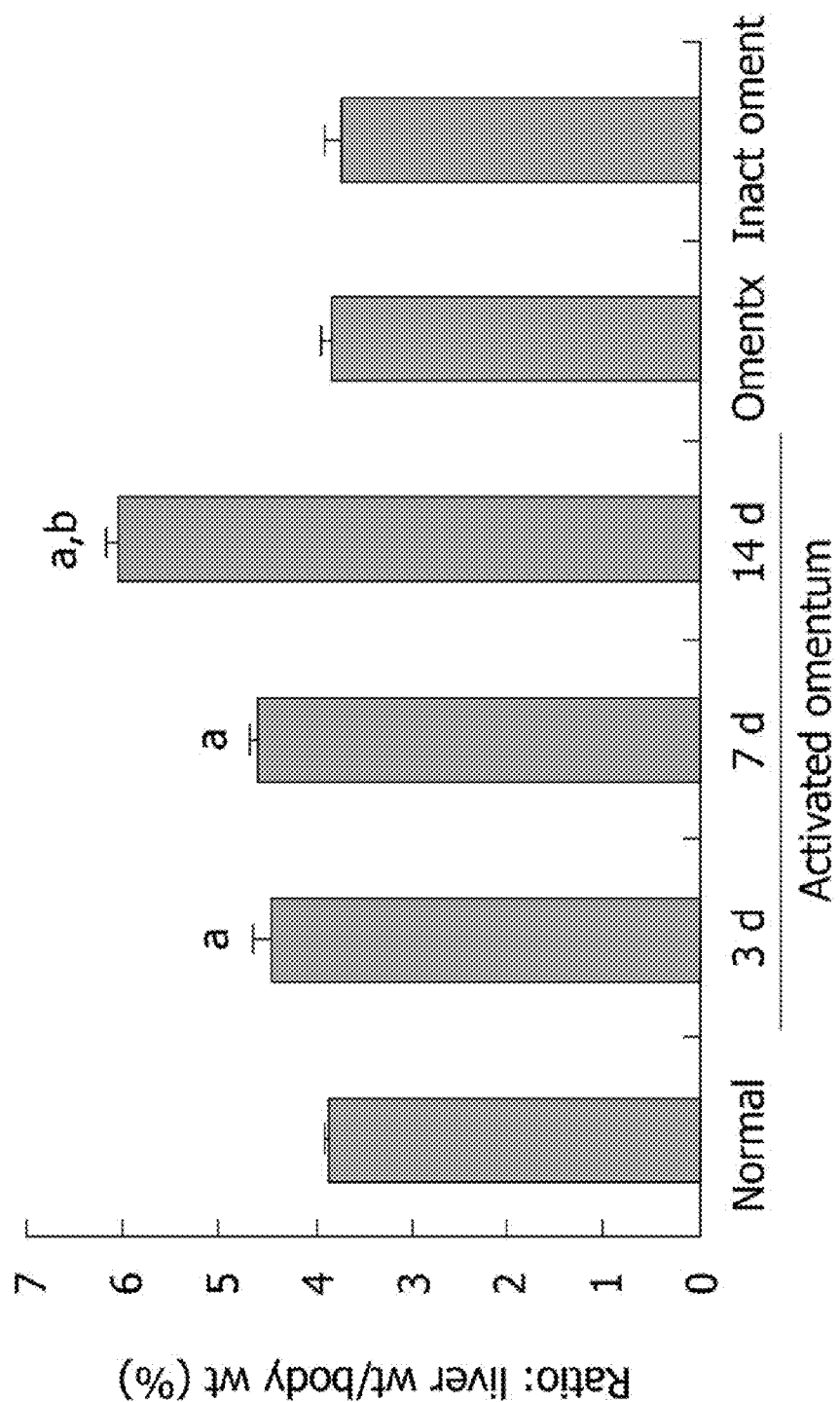
FIG. 2 shows a bar graph plotting liver mass (as a ratio of body weight) at different times after injury and fusing of an activated omentum to the wound. The ratio of liver weight to body weight in normal rats ("Normal") was established to be 3.85%±0.07%. "Omentx" identifies rats in which the omentum was removed before liver injury (n=12) and "Inact oment" identifies rats in which the liver was injured, but the omentum was inactivated (n=12). Liver regeneration following wounding and fusion of activated omentum was rapid, and by day three (3 d) the liver grew to about 110% of the original mass. The liver continued to grow, reaching a maximum size of about 150% of the original mass by day fourteen (14 d). Growth had stopped by day twenty-eight (data not shown). The investigation employed fifteen "Normal" rats and six in each of the 3 d, 7 d, 14 d and 28 d groups. An "a"

In rats with activated omentum, there was additional liver growth, especially in the wounded lobe at the point of omental attachment. There was also growth in other lobes which was suggested by alterations in the natural contours of the edges of the uninjured liver lobes. FIG. 2 shows the liver mass (as a percent ratio to body weight) at different times after wounding and fusing of the omentum to the wound. The percent ratio in normal rats was established to be 3.85±0.07 [Normal (n=15); FIG. 2]. In the activated omentum group, the liver grew to 110% of its original mass by day three (3 d) (percent ratio: 4.4±0.24) and to a maximum size of 150% by day fourteen (14 d) (percent ratio: 6.0±0.16) (n=6 at days 3, 7, 14 and 28; FIG. 2). From day fourteen to day twenty-eight (data not shown), the liver did not grow any further, but remained enlarged.

In rats with inactivated omentum, growth was observed at the site of omental fusion and filled the resected site with new tissue by day seven. However, the overall liver mass did not increase at any of the time points compared with the established normal liver mass [n=3 at days 3, 7, 14 and 28 (day 14 data shown in FIG. 2)].

In the omentectomized rats, the liver did not grow and the resection site remained visible through day twenty-eight. The percent ratio of liver to body weight in this group was similar to that of normal rats at all time points [n=3 at days 3, 7, 14 and 28 (day fourteen data shown in FIG. 2)].

In the activated omentum group, in which liver tissue grew to more than normal size, histological examination at the site of injury revealed normal hepatic architecture up to the point of omental fusion (FIG. 3B). At the site of fusion there was a wide and compact band of interlying tissue (T) between the omentum (OM) and the growing edge of the liver (L), as seen in FIG. 3B. On one side of the interlying tissue lay the liver tissue and on the other side was the omental tissue with the embedded polydextran beads. The compactness and the width of the interlying tissue was maximal between three and seven days after liver injury (400-600 µmol/L) (FIG. 3B) and became thinner (100-150 µmol/L) and less compact by day fourteen (FIG. 3C). In the interlying tissue, small islands of liver tissue, probably newly formed, were seen (FIG. 4G). By day twenty-eight, the interlying tissue was barely visible and appeared like a tissue septum (not shown).

In the inactivated omentum group in which liver growth was minimal, although the adherent omental tissue was clearly visible, an interlying tissue was observed that was thinner than that seen in the activated omentum group (FIG. 5A). In the omentectomized group, the void left by the injury was visible at all time points. The injury site lacked omental attachment, but showed a layer of dead tissue (approximately five cells thick) which sloughed off from the wound edge by day fourteen (not shown).

Immunostaining of normal adult rat liver for cytokeratin-19, a well-known marker for bile ducts as well as oval cells (oval cells are presumed to be liver stem cells), showed the expected widespread presence of oval cells in the lining of bile ducts lying in the liver triads (FIG. 4A). In the liver with or without omental attachment, cytokeratin-19 positive bile duct staining in the triads of the uninjured lobes was similar in intensity to that seen in the normal liver (not shown). In the liver tissue with activated omentum, remarkably, cytokeratin-19 positive bile ducts in the regenerated liver (day three or seven) extended into the interlying area between the liver and the omentum (FIGS. 4B-E). Occasionally, the growing edge of the liver at the interlying tissue was seen to be entirely covered with cytokeratin-19 positive cells (FIG. 4F). Islands of liver tissue, probably newly formed, were present in the interlying tissue (FIG. 4G).

In the inactivated omentum group, the interlying tissue attached to the wound edge also showed extensions of the cytokeratin-19 positive bile ducts (at days three and seven) (FIG. 5B), although these were much less frequent than those seen in the activated omentum group. In omentectomized rats, the wound edge was devoid of omental attachment, and as expected no cytokeratin-19 positive bile ducts were seen outside the liver tissue (not shown).

To further investigate if activated omentum fused to the injured liver triggered developmental events in the adult liver, the expression levels were determined for several important genes associated with pluripotent embryonic stem cell activity (Nanog, Oct-4), liver differentiation (WT1, Wnt-4, HNF-6) and fetal liver synthetic activity (α-fetoprotein; AFP) at days three and seven after wounding using RT-PCR. Comparisons between normal rat adult liver and the regenerated liver attached to the activated omentum showed high expression levels (about seven to twenty fold) of four of these genes (WT-1, Wnt-4, Nanog, AFP) in the regenerated liver tissue (FIG. 6) (Oct-4 and HNF-6 levels were negative; not shown). Wnt-4, Nanog, and AFP were maximally activated at day three, while WT-1 showed maximal activation at day seven.

Regenerated liver tissue from sites farther away from the injured area (about 0.5 cm and about 1.0 cm away from the activated omentum in the same lobe, and tissue from an uninjured lobe) showed reduced expression of WT-1, Wnt-4, and AFP genes, although still higher in all cases compared to normal adult liver (Nanog, Oct-4, AFP did not change), suggesting that the regeneration stimulus "rippled" from the injured area further into the liver tissue (data not shown).

In contrast, in the inactivated omentum group (compared to normal adult liver) the expression level of WT-1, Wnt-4 and Nanog increased to a much smaller degree than that observed in the activated omentum group at days three and seven (WT-1 by 1.5-fold, Wnt-4 by 1.9-fold and Nanog by 1.2-fold), while AFP decreased by 0.8-fold (P<0.05 in all cases; no detectable changes were seen in Oct-4 and HNF-6).

In the omentectomized group, while the expression levels of WT-1 and Nanog did not change, the levels of Wnt-4, Oct-4, AFP and HNF-6 decreased by 0.78-fold-undetectable levels compared with normal adult liver (P<0.05 in all cases).

Because liver mass can increase due to either progenitor cell activation or hepatocyte multiplication, the wedge wound experiment was also performed with a small group of rats in which hepatocyte multiplication was blocked by treatment with 2-AAF. This was performed to confirm that liver regeneration was via progenitor cells and not by hepatocyte expansion in the traumatic liver injury model. Fourteen days after wounding, 2-AAF treated rats showed complete healing of the wedge wound and increased the liver mass to 135% of the original mass [liver weight/body weight ratios: 5.1±0.2 in 2-AAF treated (n=4) versus 3.85±0.07 in normal controls (n=15); P<0.05], confirming that omentum-assisted liver regeneration was not mediated by hepatocyte expansion, but by progenitor cell activation.

The investigations described above were an attempt to regenerate liver tissue by creating a surgical wound and allowing the omentum to fuse with the wound. Whereas no liver growth was observed in the omentectomized rats, the omenta of rats with inactivated omentum were found to fuse with the injury site and, although new growth was noted, this growth did not result in a significant increase in liver mass. However, in rats with activated omentum, following omental fusion the liver grew to fill the wound and continued to grow, both at the wound site and globally, to a level of about 50% greater than the original mass. These findings suggested that the omentum plays an important role in bringing about growth and regeneration of the injured liver. The amount of liver growth induced by the omentum was proportional to the degree of omental activation, consistent with observations that the concentration of growth factors and the number of progenitor cells in the omentum increase with increased activation.

It should be noted here that the regenerative capability of the long has been long known. Experimentally, a 70% hepatectomy (either surgically or chemically) has been shown to induce a form of liver regeneration in which growth is largely due to hepatocyte proliferation. When hepatectomy is carried out following the administration of drugs that inhibit hepatocyte proliferation, the regeneration is mainly due to the expansion of oval cells. In these various models, there is a massive loss of functional liver tissue, which then systemically triggers a cascade of cytokines (such as tumor necrosis factors-α, IL-6 and growth factors). In contrast, the wedge injury used in the investigation described above was so slight that regeneration would not occur unless the omentum was activated, as evidenced by the lack of liver regeneration in the omentectomized rats.

In additional studies, attempts were made to understand the mechanism by which activation of the omentum causes liver regeneration. Histologically, at the fusion site between the activated omentum and the liver, a wide and compact interlying band of tissue was observed into which tubular structures resembling bile ducts extended and proliferated. On staining, these structures were strongly positive for cytokeratin-19, a known marker for oval cells, believed to be liver progenitor cells. At an early stage of regeneration, the oval cells in the interlying tissue were seen near small islands of liver tissue. Later these islands became integrated into the native liver, so that the border between the native and the new liver could no longer be discerned in stained sections. Because proliferation of the progenitor oval cells took place in the omentum rather than in the liver, they may have had more room to proliferate and expand, accounting for the robust, supranormal liver growth.

As genes and proteins involved in liver development (Wnt-4, WT-1, HNF-6, AFP) may become reactivated during liver regeneration, these developmental genes and also Nanog and Oct-4 (markers of early progenitor cells) were tested to see if they were altered in regenerating liver tissue. It was found that many of these genes, silent in the adult liver, were highly up-regulated (about 7 to 20-fold) after fusion of the activated omentum. Nanog was up-regulated by about 20-fold three days after omental fusion and returned to undetectable levels by day seven, suggesting the transient presence of early progenitor cells. Gene expression of Wnt-4 and AFP was highest at day three and decreased by day seven, in contrast to WT-1 which was unchanged at day three and highest at day seven. These findings were consistent with the transient activation of these transcription factors (WT-1 and Wnt-4) known to occur in liver re-modeling and differentiation. HNF-6, a marker strongly associated with hepatocyte proliferation, was unchanged, as also noted in a previous study of non-hepatocyte mediated (but progenitor cell mediated) liver regeneration. This was not surprising because liver growth by omental fusion was via oval cells and not dependent on hepatocyte proliferation. Interestingly, it was also observed that a few selected genes (WT-1, Wnt-4 and AFP) were activated in regions of the native liver about 0.5 cm and about 1.0 cm from the wound edge. The level of activation decreased as the distance from the wound edge increased, suggesting that a paracrine effect was exerted by the omentum. Importantly, lower activation levels of genes were found in the inactivated omentum group (1.2-1.9-fold), consistent with reduced liver growth seen in these rats. Furthermore, in omentectomized rats where there was no liver growth, a decrease in gene expression levels was observed compared with normal liver.

The investigations described above are believed to be the first to demonstrate the unique role of the omentum in traumatic wound healing of the liver. While previous investigations had shown that omental-derived factors stimulate wound healing and can be up-regulated by pre-activating the omentum, the present invention has shown that bringing the omentum into close contact with a liver injury causes a vigorous regeneration of liver tissue. Although the liver is known to regenerate to the original size following a significant loss of hepatic tissue, there do not appear to be any reports of liver regeneration of up to 150% of the original size, as was unexpectedly observed in the investigations described above. Because both cytokeratin-19 positive cells and expression of developmental genes were increased, it is postulated that both growth factors and stem cells are conveyed to the site of injury by omental fusion.

It is believed that contact between the omentum and damaged organs after controlled deliberate wounding may have immediate clinical applicability. Also, the use of progenitor (oval) cells isolated from the activated omentum, growth factors secreted by these cells, and stem cells cultured from activated omentum holds further promise of other exciting therapeutic possibilities. In addition to the regeneration of liver as reported above, further support for this hypothesis can be found in Singh et al., supra, which evidenced that the omentum is a source of stem cells that can be used to generate cells for in vivo therapy for human diseases, such as heart ischemia and diseases and pancreatic diseases.

Subsequent experiments have also been conducted with skin graft models with and without omental cells, and improvements in healing were observed in chronic ulcers treated with wet gauze soaked with omental cells. Medical procedures and treatments utilizing direct contact with activated omentum or utilizing such progenitor cells, growth factors, and stem cells are also likely to find application in the treatment of organ transplant recipients, Type I diabetes, lupus, multiple sclerosis (MS), rheumatoid arthritis, inflammatory bowel disease (IBD), myocarditis, vasculitis, psoriasis, sarcoidosis, Sjögren's disease, and vitiligo.

On the basis of the previously-described investigations, the healing power of the omentum can in part be attributed to the production of growth factors by omental cells. In addition, omental stem cells express several markers that are characteristic for pluripotent embryonic stem cells that may contribute to the healing mechanism. Hematopoietic stem cells are currently the best characterized adult stem cells and show a considerable heterogeneity that is in part attributable to functional diversity.

Additional investigations described below have evidenced that omental stem cells can be directly harvested from a patient or donor, or harvested as groups of heterogenous cells that attach/bind to plastic beads placed in the abdomen of a donor. Following implantation (for example, after a period of seven to ten days), the beads and binding cells can be collected. The cells can be dispersed in vitro by collagenase treatment, and then live cells can be purified and injected into the host intravenously. Whether harvested directly or collected, omental stem cells isolated from a patient's omentum offer the advantage of eliminating the concern for rejection. The omental stem cells can also be activated in vitro by T cells to enhance their immunomodulatory functions prior to in vivo injection.

The following provides a discussion of five investigations that were conducted and through which the above-noted aspects of the invention were evidenced.

In a first investigation, an omental stem cell population was analyzed for stem cell markers using flow cytometry. In FIG. 7, the majority of the cells can be seen to express CD45 and one third of this population can be seen to express CD34, suggesting that hematopoietic and mesenchymal stem cell subpopulations are located in the activated omentum. Further heterogeneity was observed by analyzing the stem cell markers Sca-1 and CD117 (c-kit). The CD34−/CD45+ population did not express CD117 but could be divided into Sca-1+ and Sca-1− cells.

Bleomycin is known to induce severe acute inflammation of the lungs, characterized by patchy aggregates of neutrophils in alveolar and interstitial spaces as well as diffuse capillary congestion and foci of intra-alveolar hemorrhages that progress to perivascular chronic inflammation with foci of lymphoid aggregates and large, early fibrosis and fibroblast proliferation. Adoptive transfer of bone marrow-derived mesenchymal stem cells is known to inhibit bleomycin-induced lung fibrosis by suppressing inflammation and by increased epithelial regeneration. While omentum cells, and particularly stromal cells and/or omentum stem cells (OSCs) are known to engraft to injured sites and promote tissue healing, whether OSCs could inhibit or prevent acute lung injury and inflammation induced by intratracheal instillation of bleomycin has not been previously described.

Whereas FIG. 8a evidences the type of injury seen in lungs twelve days after bleomycin instillation, FIG. 8b evidences a protective effect that was observed when $10^6$ OSCs were transferred by intraperitoneal injection four hours after bleomycin instillation. Adoptive transfer of OSCs can be seen in FIG. 8b to have blocked most of the inflammation and cellular accumulation observed in FIG. 8a. Only a few inflammatory areas (arrows) in the parenchyma were apparent, and injury was generally concluded to have been reduced by about 90% or more. Morphometric analysis by volume density of lesion revealed a significant difference in the extent of inflammation in the lung (FIG. 8c).

Intratracheal instillation of bleomycin is characterized by several gross changes in the diseased animals including weight loss, increase in total collagen in the lung, and severe lung inflammation. Although some of the initial weight loss may be attributed to the intratracheal instillation procedure, significant weight loss is not typically observed until after the third day of the disease, which correlates with an increase in inflammation. This parameter was used to evaluate the condition of the mice independent of histological analysis. Seven days after lung injury by bleomycin instillation, control mice lost about one to about two grams of their weight (corresponding to about 10% of starting weight). In contrast, mice that obtained OSCs gained weight during the same time period, suggesting that the lung injury was less severe and did not reduce the mouse eating pattern. The weight loss difference, plotted in FIG. 9, is highly significant ($p<0.001$).

T cells are known to be of importance to the process of fibrosis, possibly by regulating the production of cytokines and chemokines in the lung. In the absence of the costimulatory molecule CD28, the extent of fibrosis after bleomycin instillation is significantly reduced. Preliminary results presented in FIG. 10 confirm the T cell dependent development of severe acute lung injury after bleomycin instillation. Lymphocyte-deficient Rag–/– animals that were instilled with bleomycin lost significantly less weight during the following eleven days compared to wild type C57Bl/6 mice ($P=0.03$) (FIG. 10a). In addition, the extent of inflammation determined by volume density of lesion was significantly less severe in the lymphocyte-deficient animals ($P<0.01$) (FIG. 10b), whereas no difference was found in the number of cells in the bronchoalveolar fluid (FIG. 10c) and lung homogenate (data not shown).

From the investigations reported above, it can be understood that both a lack of lymphocytes and the adoptive transfer of OSCs are capable of reducing the extent of inflammation in bleomycin-injured animals, suggesting a possible influence of OSCs on lymphocytes. The effect of OSCs on activated and resting spleen T cells was therefore tested.

To determine the mechanism by which OSCs suppress bleomycin-induced lung inflammation and fibrosis, the effect of OSCs on in vitro T cell proliferation assay was investigated. Splenocytes from C57.BL/6 mice were isolated by the standard procedure, and stained with PKH26 (from Sigma), a fluorescent membrane dye that monitors cell division. T cells were stimulated by addition of anti-CD3 antibody to total splenocytes. To this culture, an equal number of OSCs from syngeneic C57/BL6 mice were added at the beginning of stimulation. After three days of co-culture, cells were analyzed by flow cytometry (FIG. 11).

When OSCs were cultured along with total splenocytes, changes were observed in the ratio between CD4 and CD8 T cells (FIG. 11a). When splenocytes were cultured alone without stimulation, the CD4:CD8 ratio was about 2:1, as observed in freshly isolated T cells (not shown). In contrast, when cells were cultured with OSCs without stimulation, this ratio changed and became 1:2, suggesting a relative increase in CD8 T cells. This appears to be caused by a mild increase of CD8 T cells since a cell number change of CD4 T cells was not observed while a mild increase was observed in CD8 T cell numbers. A slight increase of $CD4^-$ $CD8^-$ cells in splenocytes and OSC co-culture was likely due to the contribution of OSCs, although a majority of OSCs was excluded from this data by forward scatter (FSC) and side scatter (SSC) gating (shown in FIG. 11b).

Figure 12:
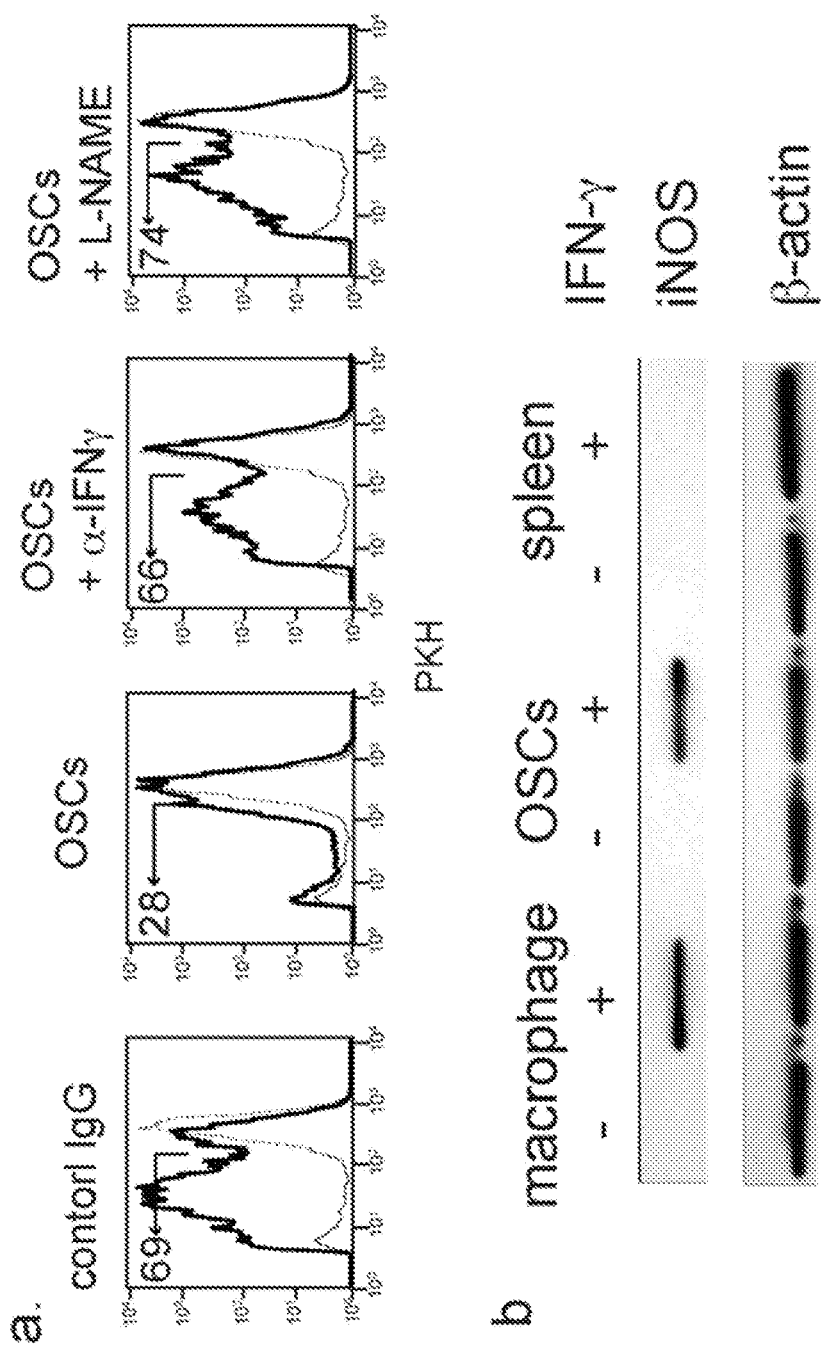

When anti-CD3 antibody and IL-2 were added to the culture, total splenocytes showed a clear sign of activation (increase of cell size, FSC and SSC, FIG. 11b), and they proliferated effectively as observed by a decrease of the level of PKH staining (FIG. 11c). Robust proliferation of both CD4 and CD8 T cells were observed (FIG. 11a). In stark contrast, when the mixture of splenocytes and OSCs were stimulated with anti-CD3 antibody, a majority of cells were dead as observed in the loss of live lymphocyte population from the FSC and SSC analysis (FIG. 11b). The remaining cells with live lymphocyte size were only 3% of total cells. Among these, CD4 and CD8 T cells were 14% and 15% respectively (FIG. 11a), substantially lower than cells stimulated without OSCs. PKH staining showed very little sign of cell division of CD4/CD8 cells, suggesting that a majority of cells that were activated by ant-CD3 stimulation died within three days of the culture with OSCs. This effect was blocked by inhibition of interferon γ (IFN-gamma) using blocking antibody (FIG. 12). The data show that OSCs acquire the ability to suppress immune responses in response to IFN-gamma. The suppressive function of OSCs require functions of inducible nitric oxide synthase (iNOS) and IFN-gamma induced expression of iNOS by OSCs. Indeed, the presence of inhibitor for iNOS blocked OSCs ability to suppress T cells (FIG. 12). Expression of iNOS was induced by IFN-gamma. From these results, it was concluded that activated T cells or factors produced by activated T cells (for example, IFN-gamma) are capable of inducing an immunoregulatory function in OSCs.

In addition to immunosuppressive functions toward adaptive immune responses (such as T cell proliferation), OSCs also showed anti-innate response function. When OSCs were added to the culture of LPS-activated macrophages, a significant suppression of tumor necrosis factor-alpha (TNF-alpha) production was observed (FIG. 13). This function of OSCs was not blocked by blockade of IFN-gamma or iNOS. Thus, it is modulated by a yet identified mechanism. OSCs ability to suppress TNF-alpha production may or may not require stimulation by TLR ligand such as LPS.

This series of investigations indicated that OSCs are capable of performing an immunomodulatory and anti-inflammatory role, a capability that is in addition to their role in the repair and/or regeneration of tissue evidenced by the first series of investigations described herein. In particular, it was concluded that OSCs should be capable of opening a new venue for treatment of lung injury, organ transplantation, and general immune and inflammatory responses, and that concern for rejection can be eliminated by treating a patient with OSCs harvested from his/her omentum.

From the above investigations, it was further concluded that activation of the omentum may not be an essential step to obtain the benefits of medical treatments using omentum cells. The investigations reported above involved the activation of omentum cells (or peritoneum-derived cells) through a first activation step entailing the in vivo injection of an inert foreign matter (e.g., beads). In the latter series of investigations, a second activation step entailed in vitro stimulation of the subsequently-harvested heterogenous omentum cells. However, this second activation step would not be necessary for clinical applications since a similar stimulation effect would be provided by in vivo immune and inflammatory responses. Moreover, the first activation step could be replaced by directly harvesting omentum, though such an approach may not be as effective because not all of the cells obtained by the first activation step were necessarily derived from omentum, and the omentum contains different type of cells that may not be obtained by direct harvesting. Therefore, an alternative method for isolation of omentum cells is believed to be possible involving the surgical removal of a portion of the omentum, isolation of non-lymphoid cells from the omentum by homogenizing tissue, and then injection of the isolated cells into a patient, with or without treatment with an activation reagent (e.g., T cells, IFN-gamma, LPS, etc.).

In view of the above, while the invention has been described in terms of specific experimental evidence and embodiments, it should be apparent that other methods and treatments could be adopted by one skilled in the art. Accordingly, it should be understood that the invention is not limited to the specific treatments and embodiments described. It should also be understood that the phraseology and terminology employed above are for the purpose of disclosing the invention and reported experiments, and do not necessarily serve as limitations to the scope of the invention. Therefore, the scope of the invention is to be limited only by the following claims.

The invention claimed is:

1. A procedure comprising in vitro activation of omental stem cells by stimulating CD45+ omental cells with activated T cells or IFN-gamma to enhance immunosuppressive functions of the omental stem cells.

2. The procedure according to claim 1, further comprising in vivo injection of the activated omental stem cells into a patient.

3. The procedure according to claim 2, wherein the procedure is performed to suppress at least one of inflammation and/or immune responses in the patient.

4. The procedure according to claim 2, wherein the CD45+ omental cells are directly harvested from the patient.

* * * * *